United States Patent
Shi et al.

(10) Patent No.: US 12,279,950 B2
(45) Date of Patent: Apr. 22, 2025

(54) CARDIAC VALVE PROSTHESIS AND DELIVERY DEVICE THEREOF

(71) Applicant: SHANGHAI MICROPORT CARDIOFLOW MEDTECH CO., LTD., Shanghai (CN)

(72) Inventors: Xingkun Shi, Shanghai (CN); Ming Yang, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 988 days.

(21) Appl. No.: 16/966,008

(22) PCT Filed: Jan. 11, 2019

(86) PCT No.: PCT/CN2019/071292
§ 371 (c)(1),
(2) Date: Jul. 30, 2020

(87) PCT Pub. No.: WO2019/149046
PCT Pub. Date: Aug. 8, 2019

(65) Prior Publication Data
US 2020/0352712 A1    Nov. 12, 2020

(30) Foreign Application Priority Data

Feb. 1, 2018  (CN) .......................... 201810103244.0

(51) Int. Cl.
*A61F 2/24*  (2006.01)

(52) U.S. Cl.
CPC .......... *A61F 2/2418* (2013.01); *A61F 2/2409* (2013.01); *A61F 2/2427* (2013.01);
(Continued)

(58) Field of Classification Search
CPC .... A61F 2/2418; A61F 2/2409; A61F 2/2427; A61F 2210/0004; A61F 2220/0016;
(Continued)

(56) References Cited

U.S. PATENT DOCUMENTS 7,959,670 B2    6/2011  Bolduc
8,551,161 B2 *  10/2013 Dolan ................... A61F 2/2466
                                                        623/1.14
(Continued)

FOREIGN PATENT DOCUMENTS

CN    1308512 A     8/2001
CN    1870949 A    11/2006
(Continued)

OTHER PUBLICATIONS

Japanese Office Action for Japanese Application No. 2020-564300, dated Nov. 30, 2021 with translation, 12 pages.
(Continued)

*Primary Examiner* — Leslie A Lopez
*Assistant Examiner* — Aren Patel
(74) *Attorney, Agent, or Firm* — NSIP Law

(57) ABSTRACT

A cardiac valve prosthesis, comprising: an expandable valve support provided with multiple fixing holes, an artificial valve provided on the valve support, and a thorn structure comprising an expandable thorn support and multiple thorns. The multiple thorns are provided on the thorn support, and are used for, when the cardiac valve prosthesis is implanted into a cardiac chamber, passing through the multiple fixing holes and penetrating tissue in the cardiac chamber so as to fix the valve support. The thorn structure and the valve support are provided independent of each other so that separate manufacturing and processing thereof can be achieved, and the thorn structure and the valve support work together in a non-connected manner so as to
(Continued)

facilitate step-by-step load and release, such that the size of a delivery catheter and the length of the valve support can be effectively reduced, the risk of breakage is reduced, and it also facilitates recovery when the cardiac valve prosthesis is not released in place.

18 Claims, 7 Drawing Sheets

(52) U.S. Cl.
CPC ............... *A61F 2210/0004* (2013.01); *A61F 2220/0016* (2013.01); *A61F 2230/0067* (2013.01); *A61F 2230/0086* (2013.01)

(58) Field of Classification Search
CPC ...... A61F 2230/0067; A61F 2230/0086; A61F 2/24; A61F 2/2412
See application file for complete search history.

(56) References Cited

U.S. PATENT DOCUMENTS

| | | | |
|---|---|---|---|
| 2002/0198586 A1* | 12/2002 | Inoue | A61F 2/966 623/1.13 |
| 2007/0049866 A1 | 3/2007 | Schwartz et al. | |
| 2008/0208329 A1* | 8/2008 | Bishop | A61B 17/10 623/2.11 |
| 2008/0275550 A1 | 11/2008 | Kheradvar et al. | |
| 2011/0276091 A1 | 11/2011 | Melanson et al. | |
| 2012/0035712 A1* | 2/2012 | Maisano | A61F 2/915 623/2.11 |
| 2012/0109289 A1 | 5/2012 | Bolling | |
| 2014/0052169 A1 | 2/2014 | Schwartz et al. | |
| 2014/0303719 A1* | 10/2014 | Cox | A61F 2/2445 623/2.37 |
| 2015/0066136 A1 | 3/2015 | Smith et al. | |
| 2015/0148896 A1* | 5/2015 | Karapetian | A61F 2/07 623/2.11 |
| 2016/0235525 A1* | 8/2016 | Rothstein | A61F 2/2418 |
| 2019/0105153 A1* | 4/2019 | Barash | A61F 2/2418 |
| 2019/0142582 A1* | 5/2019 | Drasler | A61F 2/2418 623/2.11 |
| 2019/0336279 A1* | 11/2019 | Liu | A61F 2/2418 |
| 2021/0030535 A1* | 2/2021 | Liu | A61F 2/2418 |

FOREIGN PATENT DOCUMENTS

| | | |
|---|---|---|
| CN | 104055603 A | 9/2014 |
| CN | 106618802 A | 5/2017 |
| CN | 107496055 A | 12/2017 |
| JP | 2007508894 A | 4/2007 |
| JP | 2016509880 A | 4/2016 |
| WO | 2013059747 A1 | 4/2013 |
| WO | 2013088327 A1 | 6/2013 |
| WO | 2016196270 A1 | 12/2016 |

OTHER PUBLICATIONS

Japanese Office Action for Japanese Application No. 2020-564300, dated Jul. 12, 2022 with translation, 12 pages.
European Communication pursuant to Article 94(3) for European Application No. 19 747 473.7, dated Jul. 7, 2022, 6 pages.
Extended European Search Report for European Application No. 19 747 473.7, dated Oct. 6, 2021, 6 pages.
Notice of Allowance for Application No. 2020-564300, dated Jan. 24, 2023 with translation, 6 pages.

\* cited by examiner

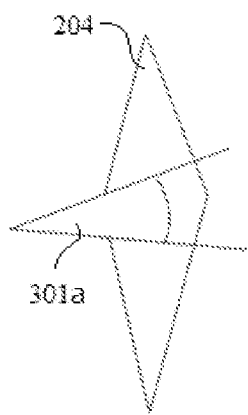 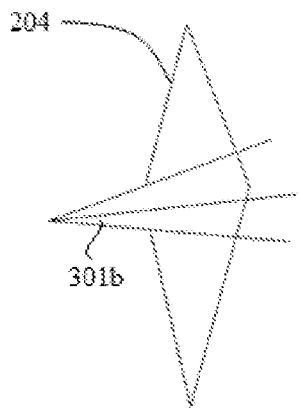 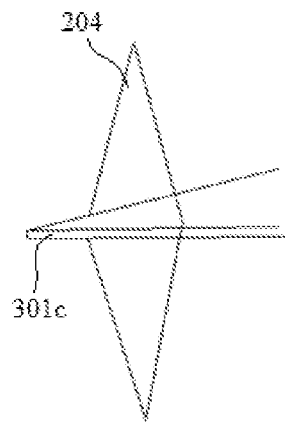
Fig. 4a	Fig. 4b	Fig.4c
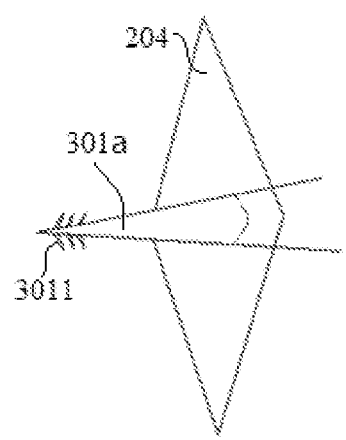
Fig. 5

CARDIAC VALVE PROSTHESIS AND DELIVERY DEVICE THEREOF

CROSS-REFERENCE TO RELATED APPLICATIONS

This application is a continuation of International Application No. PCT/CN2019/071292, filed on Jan. 11, 2019, which claims to the Chinese Application No. 201810103244.0, filed on Feb. 1, 2018. The disclosures of both applications are hereby incorporated by reference in their entireties.

FIELD

The present disclosure relates to the field of medical device, in particular relates to a cardiac valve prosthesis and delivery device thereof.

BACKGROUND

At present, transcatheter mitral valve replacement (tmvr) has become a research hotspot at home and abroad, but there are some core problems, such as large stent size, left ventricular outflow tract interference, and anchorage difficulties. In order to solve the problem of valve anchoring of large-scale mitral valve stent, some foreign companies have taken different attempts, such as the intrepid mitral valve of Medtronic company, which uses the anchoring thorns on the stent to fix the valve; for example, the CardiAQe mitral valve of Edward company, which uses the way of hooking the original mitral valve leaf to anchor the prosthesis; such as Highlife company's interventional valve uses an additional anchor ring to bind the prosthesis to the primary leaflet. Generally speaking, the way of using the prick anchorage is simple to operate and little affected by the difference of anatomy. However, there are still following problems: the valve stent and the prick structure are made in one, which makes the crooked and protruding prick structure not only limit the size of the delivery catheter and the length of the valve stent, but also easily lead to the failure of the anchorage caused by the fracture of the prick anchorage, and hinder the recovery of the valve when the release is not in place.

SUMMARY

Based on this, it is necessary to provide a cardiac valve prosthesis, a delivery device and a method for loading and releasing the cardiac valve prosthesis, by setting the valve stent and the thorn structure independently, the size of the delivery device and the length of the valve stent can be reduced, so that the risk of fracture can be reduced, and the valve can be recovered when the release is not in place.

A cardiac valve prosthesis, comprising: an expandable valve stent provided with multiple fixing holes; an artificial valve provided on the valve stent; and a thorn structure comprising an expandable thorn stent and multiple thorns; and the multiple thorns are provided on the thorn stent, and are used for, when the cardiac valve prosthesis is implanted into a cardiac chamber, passing through the multiple fixing holes and penetrating tissue in the cardiac chamber so as to fix the valve stent.

The above mentioned cardiac valve prosthesis, by setting the valve stent and the thorn structure independently, can be manufactured and processed separately, and can cooperate with each other by no connecting way, so as to facilitate the loading and release step by step, further the size of the delivery device and the length of the valve stent can be reduced, the risk of fracture can be reduced, and the cardiac valve prosthesis can be recovered when the release is not in place.

In an alternative embodiment, the size of the thorn stent in the fully expanded state is greater than or equal to the size of the valve stent in the fully expanded state.

In an alternative embodiment, the thorn structure further comprising: a thorn lug provided at the proximal end of the thorn stent and extended toward the central axis of the thorn stent; and the multiple thorns provided at the distal end of the thorn stent and extended away from the central axis of the thorn stent.

In an alternative embodiment, the tips of the multiple thorns are conical tips, pyramid tips or prismatic tips.

In an alternative embodiment, wherein the tips of the multiple thorns provided with multiple barb structures.

In an alternative embodiment, the material of the multiple thorns is medical biodegradable material.

In an alternative embodiment, the medical biodegradable material comprising at least one of polycaprolactone, polylactic acid and polyglycolic acid copolymer.

In an alternative embodiment, the thorn stent comprising: multiple connecting rods connected end to end to form a closed chain structure; and any two adjacent connecting rods form a V-shaped structure.

In an alternative embodiment, the multiple thorns and the thorn lug are respectively provided at the connection between any two of the multiple connecting rods.

In an alternative embodiment, the multiple thorns and the multiple connecting rods are an integral manufacturing structure.

In an alternative embodiment, the thorn stent is a mesh structure composed of multiple diamond-shaped grids.

In an alternative embodiment, the multiple fixing holes comprising dense grids arranged along the circumferential direction of the valve stent, and the size of the dense grids is smaller than that of other grids on the valve stent.

In an alternative embodiment, the size of the dense grids is ⅓ to ⅙ of that of other grids on the valve stent.

In an alternative embodiment, the position of the multiple thorns on the thorn stent matches the position of the fixing holes on the valve stent, and the size of the multiple thorns on the thorn stent is smaller than the size of the fixing holes on the valve stent.

In an alternative embodiment, the valve stent comprising an inflow channel part for blood inflow and an outflow channel part for blood outflow; and the multiple fixing holes are provided in the inflow channel part or at the junction of the inflow channel part and the outflow channel part; and the multiple fixing holes are distributed along the circumferential direction of the valve stent.

A delivery device for loading the cardiac valve prosthesis of any of the above items, wherein the delivery device comprising: a conical head; a control handle; a delivery catheter, the two ends of the delivery catheter are respectively connected with the conical head and the control handle; and the delivery catheter comprising a first catheter assembly and a second catheter assembly sleeved outside the first catheter assembly, the first catheter assembly is used for loading the thorn structure, the second catheter assembly is used for loading the valve stent; and the control handle is used to control the first catheter assembly to release the thorn structure in the process of controlling the second catheter assembly to release the valve stent, so that the thorn structure can penetrate the tissues in the cardiac cavity through the multiple fixing holes to fix the valve stent.

The above mentioned delivery device, can realize the loading and releasing operation of the thorn structure and the valve stent step by step using the delivery catheter formed by the first catheter assembly and the second catheter assembly, further can improve the fixation strength and accuracy of the cardiac valve prosthesis, at the same time, it is convenient for the operator to operate, and it is also convenient for recovery when the release of the cardiac valve prosthesis is not in place.

In an alternative embodiment, the control handle comprising a first control part and a second control part, the first control part is connected with the first catheter assembly for controlling the first catheter assembly, the second control part is connected with the second catheter assembly for controlling the second catheter assembly.

In an alternative embodiment, the first catheter assembly comprising: a soft catheter; a thorn external catheter, the proximal end of the thorn external catheter is connected to the first control part; a thorn inner catheter provided inside the thorn external catheter, and the proximal end of the thorn inner catheter is connected to the first control part; a first fixing head, one end of the first fixing head is connected to the thorn inner catheter, the other end is connected to the conical head through the soft catheter; and the first fixing head is used for loading the thorn structure.

In an alternative embodiment, the first control part comprising: a first control structure connected with the thorn external catheter for controlling the movement of the thorn external catheter relative to the thorn inner catheter.

In an alternative embodiment, the second catheter assembly comprising: a valve stent external catheter, the proximal end of the valve stent external catheter is connected with the second control part; a valve stent inner catheter provided inside the valve stent external catheter, and the proximal end of the valve stent inner catheter is connected with the second control part; a second fixing head fixedly connected with the valve stent inner catheter; and the second fixing head is used for loading the valve stent.

In an alternative embodiment, the second control part comprising: a second control structure connected with the valve stent external catheter for controlling the movement of the valve stent external catheter relative to the valve stent inner catheter.

BRIEF DESCRIPTION OF FIGURES

FIGS. 4a-4c are schematic views illustrating different shapes of thorn tips passing through fixing holes.

FIG. 5 is a schematic view illustrating a thorn tip with a barb structure passing through a fixing hole.

DETAILED DESCRIPTION

Embodiments of the present disclosure will be further described in detail below in combination with the drawings and embodiments. It should be understood that the specific embodiments described herein are only used to interpret the present disclosure and are not used to define the present disclosure.

The present disclosure uses schematic diagrams for detailed description, but these schematic diagrams are only for the convenience of detailing examples of the present disclosure, and should not be regarded as the limitation of the present disclosure. As used in the specification and the appended claims, the singular forms "a", "one" and "the" include plural objects, unless the content otherwise expressly indicates. As used in this specification and the appended claims, the term "or" is generally used to include the meaning of "and/or", unless the content otherwise expressly indicates. The term "proximal end" usually refers to the end close to the operator, "distal end" refers to the end far away from the operator.

Figure 1:
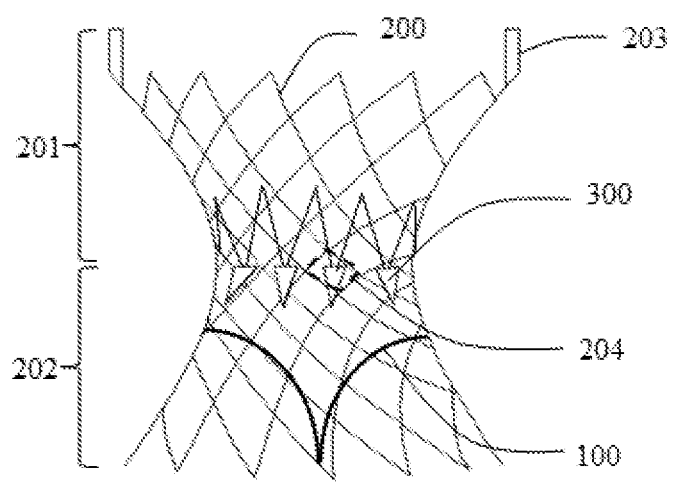
FIG. 1 is a schematic view illustrating the structure of the cardiac valve prosthesis according to one embodiment of this disclosure.

FIG. 1 is a schematic view illustrating the structure of the cardiac valve prosthesis according to one embodiment of this disclosure. As shown in FIG. 1, an expandable valve stent comprising an expandable artificial valve (i.e. valve leaf) 100, an expandable valve stent 200 and a thorn structure 300, the artificial valve is provided on the valve stent 200. Multiple fixing holes 204 are provided on the valve stent 200, wherein the thorn structure 300 can pass through the multiple fixing holes 204 and penetrate tissue in the cardiac chamber so as to fix the valve stent 200 at a preset position when the cardiac valve prosthesis is implanted into a cardiac chamber, so that the artificial valve 100 can replace human tissues such as mitral valve to work, so as to achieve the purpose of treating mitral valve disease.

In one embodiment, as shown in FIG. 1, the valve stent 200 is a tubular expandable structure, which is easy to be loaded into the delivery device during compression. When the valve stent 200 is implanted into the human body through the delivery device and released, the valve stent 200 can be expanded to a preset size to play a supporting role. The valve stent 200 comprising an inflow channel part 201 and an outflow channel part 202, the inflow channel part 201 can be used as a channel for blood to flow into the cardiac valve prosthesis, and the outflow channel part 202 can be used as a channel for blood to flow out of the cardiac valve prosthesis. After the cardiac valve prosthesis is implanted, the inflow channel part 201 is located at the left atrial end, the outflow part 202 is located at the left ventricular end, and the thorn structure 300 can be inserted into the mitral valve ring to fix the valve stent 200.

The artificial valve 100 can be made of biological materials such as bovine pericardium, horse pericardium or pig pericardium, and the artificial valve 100 can be sutured (such as three valve leaf suture) and fixed on the valve stent 200 by the suturing process, that is to say, in normal operation, the blood flows from the left atrium through the inflow channel part 201 by the artificial valve 100, and through the outflow channel part 202 into the left ventricle.

Further, as shown in FIG. 1, in order to make the thorn structure 300 more stable for fixing the valve stent 200, the multiple fixing holes 204 can be provided in the inflow channel part 201 or the junction of the inflow channel part 201 and the outflow channel part 202. At the same time, in order to further improve the stability and operation convenience, the multiple fixing holes 204 can be evenly distributed along the circumference. The valve stent 200 can further be a dumbbell structure, that is, the opening at both ends is large and the middle part is small, and the diameter at the junction of the inflow channel part 201 and the outflow channel part 202 is smaller than the port diameter of the outflow channel part 202 and the inflow channel part 201. Further, the port diameter of the inflow channel part 201 is bigger than the port diameter of the outflow channel part 202. The port diameter 201 of the inflow channel part 201 can be 40 mm-70 mm (such as 40 mm, 45 mm, 50 mm, 55 mm, 65 mm or 70 mm, etc.), the port diameter of the outflow channel part 202 can be 35 mm-60 mm (such as 35 mm, 39 mm, 44 mm, 49 mm, 54 mm or 60 mm, etc.), the diameter at the junction of the inflow channel part 201 and the outflow channel part 202 can be 30 mm-59 mm (such as 30 mm, 34 mm, 38 mm, 42 mm, 53 mm or 59 mm etc.).

Further, as shown in FIG. 1, the valve stent 200 can be a tubular diamond-shaped grids structure prepared by weaving or cutting with shape memory alloy such as nickel titanium alloy, so as to facilitate compression into a smaller diameter delivery catheter during implantation. For example, 6~24 grids (such as 6, 8, 12, 16, 20 or 24 grids) are provided along the circumferential direction of the valve stent 200, 3~8 rows of grids are provided along the axial direction. In order to make the valve stent 200 more stable, the size and shape of each grid in the same circumferential direction can be set to be the same, so that the expanded valve stent 200 has a circular grid evenly distributed in the circumferential direction, further improving the radial support force of the valve stent 200, that is to say, when the valve stent 200 is expanded, the primary valve leaf can be opened, and the artificial valve 100 can be fixed at the preset position by the thorn structure 300 to fix the expanded valve stent 200. In one embodiment, the multiple fixing holes 204 can be dense grids arranged along the circumferential direction of the valve stent 200, and the size of the each dense grid is smaller than that of other grids on the valve stent 200. In order to ensure that the thorn structure 300 has a better fixing effect, the size of the dense grids can be ⅓ to ⅙ of that of other grids on the valve stent 200.

Multiple thorn lugs 203 of valve stent for loading are provided at the opening end of the inflow channel part 201, and fillet can be used for smooth transition between different grids (such as grids of the valve stent 200, dense grids, grids of the valve stent 200 and dense grids) of the valve stent 200, and the radius of fillet can be 0.03 mm-0.3 mm (such as 0.03 mm, 0.05 mm, 0.1 mm, 0.15 mm, 0.25 mm or 0.3 mm etc.).

Figure 2:
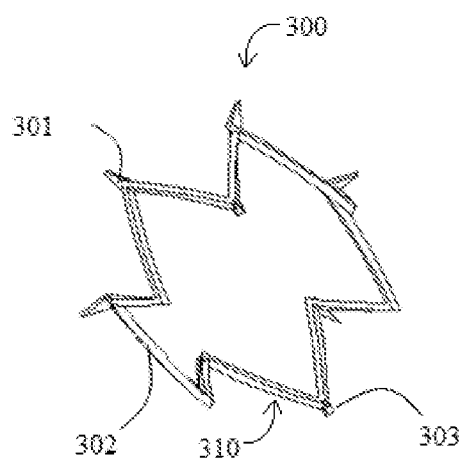
FIG. 2 is a schematic view illustrating the thorn structure in FIG. 1.

FIG. 2 is a schematic view illustrating the thorn structure in FIG. 1. As shown in FIG. 1 and FIG. 2, based on the above mentioned embodiment, the thorn structure 300 comprising a thorn stent 310 and multiple thorns 301, and the multiple thorns 301 are fixedly provided on the thorn stent 310, so that when the cardiac valve prosthesis is implanted, the multiple thorns 301 penetrates the multiple fixing holes 204 one by one correspondingly into the human tissue, and the valve stent 200 is fixed with the thorn stent 310. In one embodiment, the thorn stent 310 comprising multiple connecting rods 302, the multiple connecting rods 302 connected end to end to form a closed chain structure as shown in FIG. 2, and any two adjacent connecting rods form a V-shaped structure. Of course, in other embodiments, the thorn stent 310 may also be a mesh structure composed of multiple diamond-shaped grids, which is not limited by the present disclosure.

The thorn stent 310 can also be expandable structure, may be made of shape memory alloy material, such as nickel titanium alloy, to facilitate compression and loading into the delivery device, and release when the cardiac valve prosthesis is implanted. The thorns 301 provided on the thorn stent 310 is pierced into the cardiac cavity tissue through the above-mentioned fixing holes from the inside of the expanded valve stent 200, and then the valve stent 200 is fixed.

In one embodiment, as shown in FIG. 2, in the above-mentioned thorn structure 300, a thorn 301 can be provided at the end connection of two adjacent connecting rods 302, and the tip of the thorn 301 may protrude out of the thorn stent 310, toward the external area of the thorn stent 310, so as to be inserted and fixed in the cardiac cavity tissue through the fixing hole 204. In one embodiment, the size of the thorn stent 310 in the fully expanded state is greater than or equal to the size of the valve stent 200 in the fully expanded state. The position of the thorn 301 on the thorn stent 310 matches the position of the fixing hole 204 on the valve stent 200, and the size of the thorn 301 on the thorn stent 310 is smaller than the size of the fixing hole 204 on the valve stent 200, so that the thorn 301 can smoothly pass through the fixing hole 204 on the valve stent 200, inserted into human cardiac cavity tissue for internal fixation.

Figure 3:
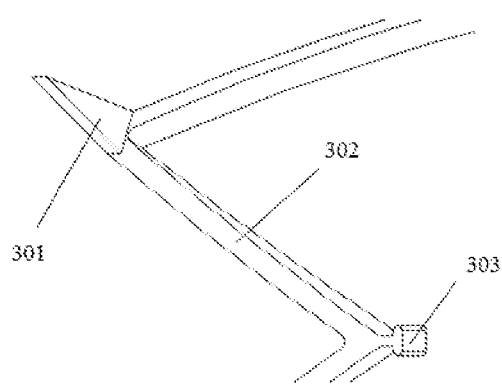
FIG. 3 is a partial enlarged schematic view illustrating the thorn structure in FIG. 2.

FIG. 3 is a partial enlarged schematic view illustrating the thorn structure in FIG. 2. As shown in FIG. 3, in an alternative embodiment, the connecting node of the connecting rod 302 can be provided with a thorn 301 and a thorn lug 303, the thorn 301 is provided at the distal end of the thorn stent 310, and the thorn lug 303 is provided at the proximal end of the thorn stent 310. Further, the thorn lug 303 and the thorn 301 can be provided in intervals at different connecting nodes of the thorn stent 310, and the thorn 301 extends in the direction away from the central axis of the thorn stent 310, while the thorn lug 303 extends in the direction close to the central axis of the thorn stent 310, so as to facilitate the loading and release of the thorn structure 300. For example, as shown in FIGS. 1~3, multiple fixing holes 204 are uniformly distributed in the circumferential direction of the expanded valve stent 200, while multiple thorns 301 are provided in the position of the fixing holes 204 corresponding to the expanded thorn stent 310, and 2-6 thorn lugs 303 are evenly provided in the expanded thorn stent 310.

Further, FIGS. 4a~4c are schematic views illustrating different shapes of thorn tips passing through fixing holes. FIG. 5 is a schematic view illustrating a thorn tip with a barb structure passing through a fixing hole. As shown in FIGS. 4a~4c and FIG. 5, one end of the thorn 301 is a free end, the other end of the thorn 301 is a non-free end, and the free end of the thorn 301 is a tip. For example, the tip of the thorn 301 can be a conical tip 301a shown in FIG. 4A, a pyramidal tip 301b shown in FIG. 4B and/or a prismatic tip 301c shown in FIG. 4C, etc., and in order to further improve the fixation performance of the thorn 301, barb structures 3011 shown in FIG. 5 can also be provided at the tip of the thorn 301.

As shown in FIGS. 2-3, the thorn 301 and the connecting rod 302 can be manufactured integrally to reduce the manufacturing cost and the process difficulty. For example, shape memory metals such as nickel titanium alloy can be used to manufacture the thorn structure 300 by cutting and other processes, or traditional metal materials such as stainless steel, polymer materials, degradable materials can be used to manufacture the thorn structure 300. In one embodiment, because the thorn structure 300 is mainly fixed in the early stage of prosthesis implantation, when the valve stent 200 is wrapped by endothelium in the later stage, the thorn 301 will lose its original localization function, and the remaining thorn structure 300 will cause permanent trauma to the valve ring tissue. In order to reduce the many complications caused by the residual thorn 301, the thorn 301 and the connecting rod 302 can be manufactured separately, and the thorn structure 300 can be formed through such welding or mechanical cooperation connection, so as to facilitate the removal of the thorn 301 at the later stage of prosthesis implantation. For example, at least one or more degradable medical biomaterials, such as polycaprolactone, polylactic acid or polyacetic glycolic acid copolymer, can be used to prepare the thorn 301, while metal or polymer materials, such as nickel titanium alloy and stainless steel, can be used to manufacture the connecting rod 302, so that the connecting rod 302 can maintain the existing supporting role, while the thorn 301 is used for fixation in the early stage of prosthesis implantation In the later stage, it will degrade automatically to avoid the complications caused by the residual thorn 301.

In practical application, when the valve prosthesis is implanted into the human body, the valve stent 200 can be released and implanted first, and then the thorn structure 300 can be released inside the expanded valve stent 200, so that the thorn 301 can penetrate the fixing hole 204 on the valve stent 200 and penetrate into the primary valve ring and/or valve leaf of the patient, so that the valve stent 200 can be fixed at the preset position without loosening. In one embodiment, when the valve stent 200 is fixed at a preset position, the artificial valve leaf may be located below the thorn 301. For example, the axial distance between the highest point of the valve leaf and the thorn 301 is 0-10 mm, in one embodiment, 3-6 mm.

The valve prosthesis in the above-mentioned embodiment, because the thorn structure 300 and the valve stent 200 are manufactured separately, and the valve prosthesis is fixed based on the step by step loading and release and mechanical cooperation, so as to avoid the fracture and fall off of the thorn structure made in one body, and cause complications such as thrombus, stem plug, etc. At the same time, the separately manufactured thorn structure and valve stent can also freely choose the direction of the turning of the thorn 301 according to the actual situation, which is conducive to the recovery of the valve, and the degradable material of the thorn can effectively avoid the permanent damage to the tissue, and facilitate the re-implantation of the same type of valve prosthesis.

Figure 6:
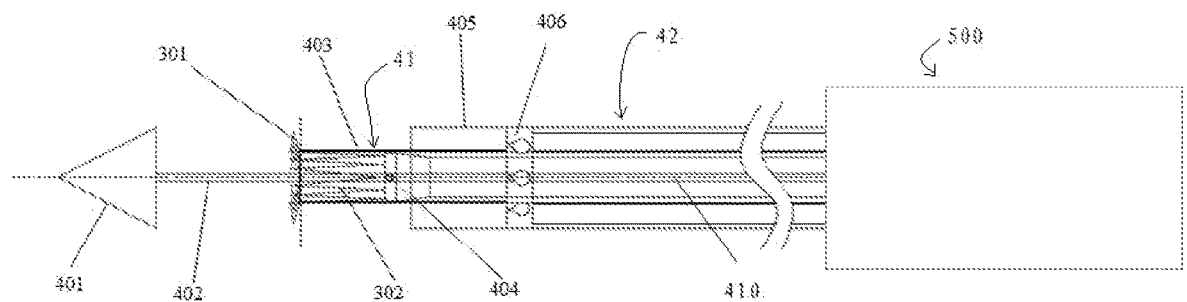
FIG. 6 is a schematic view illustrating the structure of the front end part after the thorn structure is loaded in the delivery device according to one embodiment of this disclosure.
Figure 8:
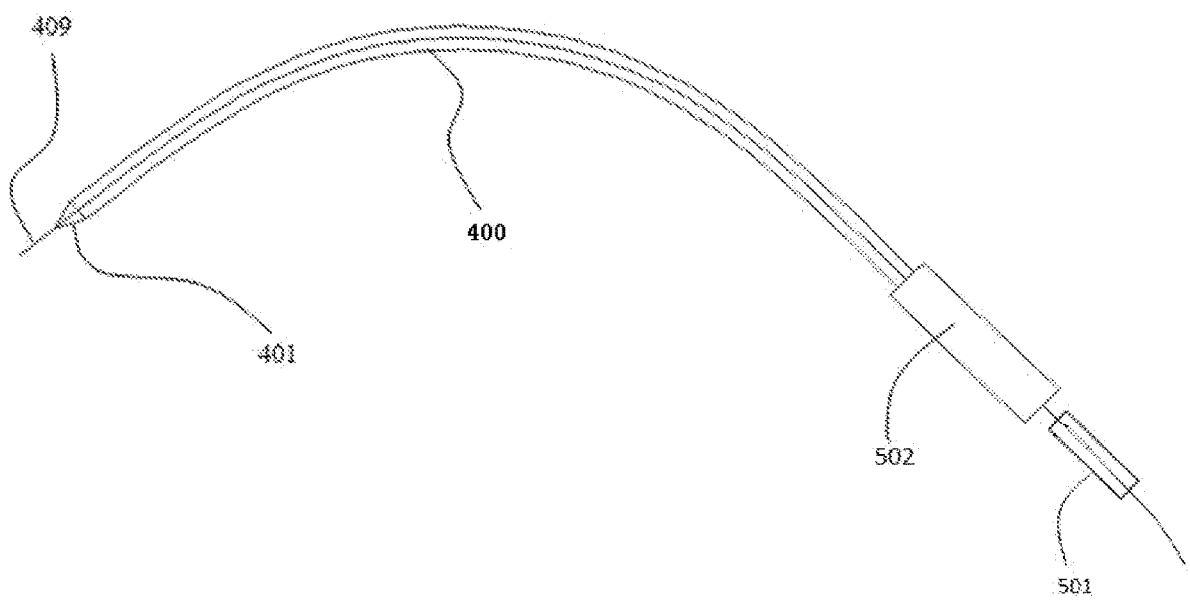
FIG. 8 is a schematic view illustrating the overall structure after the thorn structure and the valve stent are loaded in the delivery device in FIG. 6.

FIG. 6 is a schematic view illustrating the structure of the front end part after the thorn structure is loaded in the delivery device according to one embodiment of this disclosure. FIG. 8 is a schematic view illustrating the overall structure after the thorn structure and the valve stent are loaded in the delivery device in FIG. 6. As shown in FIGS. 6 and 8, the delivery device in the embodiment can be used to load any valve prosthesis in the above-mentioned embodiment. The delivery device can be composed of multiple nested delivery catheters, In one embodiment comprising a conical head 401, a control handle 500 and a delivery catheter 400. The proximal end of the delivery catheter 400 is connected with the control handle 500, and the distal end of the delivery catheter 400 is connected with the conical head 401.

Figure 7:
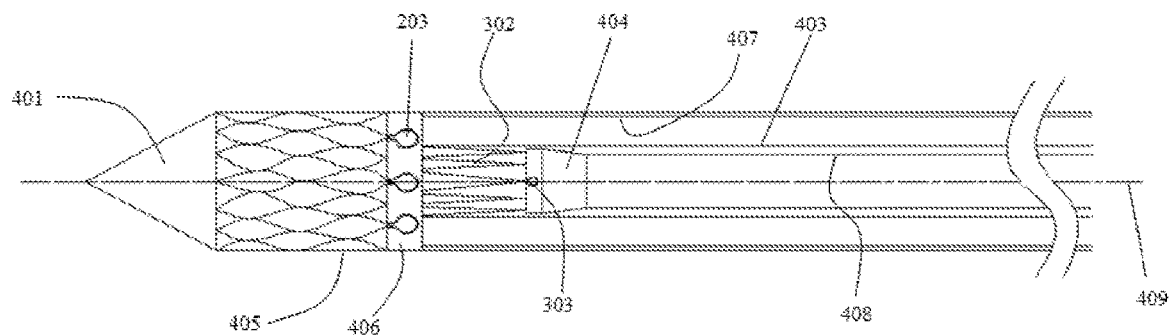
FIG. 7 is a schematic view illustrating the structure of the front end part after the thorn structure and the valve stent are loaded in the delivery device in FIG. 6.

In one embodiment, as shown in FIG. 6 and FIG. 7, the delivery catheter 400 comprising a first catheter assembly 41 and a second catheter assembly 42 sleeved outside the first catheter assembly 41, the first catheter assembly 41 can be used to load and deliver the thorn structure 300, the second catheter assembly 42 can be used to load and deliver valve stent 200. The control handle 500 is used to control the second catheter assembly 42 to release the valve stent 200 and control the first catheter assembly 41 to release the thorn structure 300 after the valve stent 200 is expanded, So that the thorn 301 in the thorn structure 300 is pierced into the human tissue through the fixing hole 204 on the valve stent 200, so as to fix the valve stent 200 at a preset position, so that the artificial valve 100 can work instead of the original valve leaf.

The first catheter assembly 41 is provided inside the second catheter assembly 42. Correspondingly, the control handle 500 comprising a first control part 501 and a second control part 502, the first control part 501 is connected with the first catheter assembly 41 for controlling the first catheter assembly 41, the second control part 502 is connected with the second catheter assembly 42 for controlling the second catheter assembly 42.

In the above-mentioned embodiment, because the thorn structure 300 and the valve stent 200 are manufactured and loaded respectively, the diameter of the delivery catheter 400 and the height of the valve stent 200 can be reduced, so as to facilitate the atrial septal approach. It is convenient for catheters to be implanted into human body through femoral vein, right atrium through vein, and left atrium through ovum puncture, so as to reduce the trauma to human tissue.

As shown in FIGS. 6-10, in an alternative embodiment, the first catheter assembly 41 comprising a soft catheter 402, a first fixing head, a thorn external catheter 403, a thorn inner catheter 408 and an inner core catheter 410. In one embodiment one end of the first fixing head 404 is respectively connected with the thorn inner catheter 408 and the inner core catheter 410, the inner core catheter 410 is provided in the thorn inner catheter 408, and the other end of the inner core catheter 410 can be connected to the first control part 501. Another end of the fixing head 404 is connected to the conical head 401, the thorn inner catheter 408 is provided inside the thorn external catheter 403, so that the thorn external catheter 403 is sleeved on the thorn inner catheter 408, and the proximal ends of the thorn external catheter 403 and the thorn inner catheter 408 are respectively connected with the first control part 501. When the first control part 501 moves, the thorn external catheter 403 and the thorn inner catheter 408 can be driven to move synchronously. In one embodiment, the first control unit 501 also has a first control structure 501a, which is used to connect with the thorn external catheter 403, so as to control the movement of the thorn external catheter 403 relative to the thorn inner catheter 408. The first control structure 501a can be a knob, which is connected with the thorn inner catheter 408 through a worm wheel structure. Of course, those skilled in the art can also use other mechanical or electric structures to control the thorn external catheter 403, which is not limited by the present disclosure.

As shown in FIGS. 6-8, the second catheter assembly 42 comprising a second fixing head 406, a valve stent external catheter 405 and a valve stent inner catheter 407. In one embodiment, the proximal ends of the valve stent external catheter 405 and the valve stent inner catheter 407 are respectively connected with the second control part 502. The valve stent inner catheter 407 is provided inside the valve stent external catheter 405, that is, the valve stent external catheter 405 is provided on the valve stent inner catheter 407. The second fixing head 406 is fixedly connected with the valve stent inner catheter 407. The second control part 502 also has a second control structure 502a for connecting with the valve stent external catheter 405, so as to control the movement of the valve stent external catheter 405 relative to the valve stent inner catheter 407. The second control structure 502a can be a knob, which is connected with the valve stent inner catheter 407 through a worm gear structure. Of course, those skilled in the art can also use other mechanical structures or electric structures to realize the control of the valve stent external catheter 405, which is not limited by the present disclosure.

Figure 10:
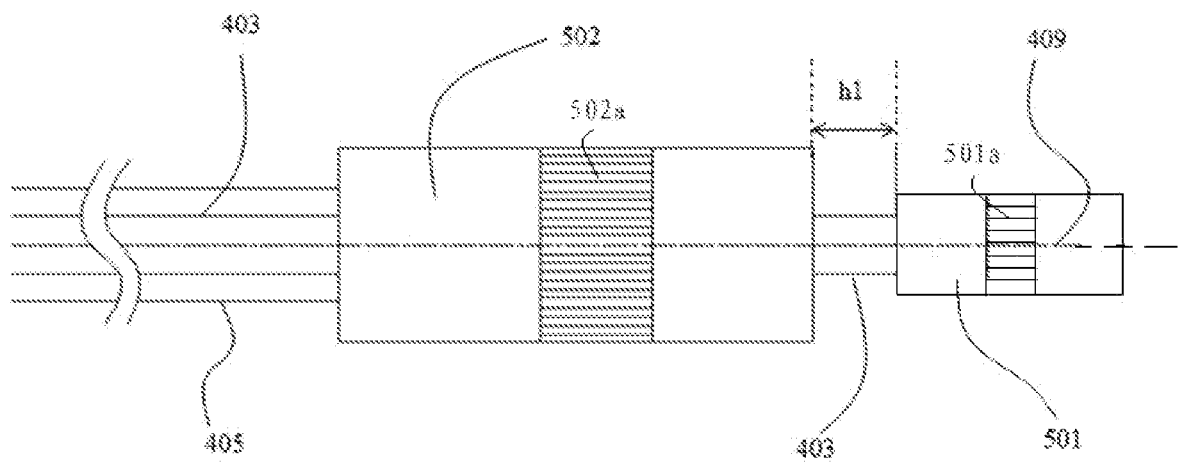
FIG. 10 is a schematic view illustrating the structure of the control handle of the delivery device according to one embodiment of the disclosure.

As shown in FIG. 10, the thorn external catheter 403 and the thorn inner catheter 408 are connected to the first control part 501 through the second control part 502, and the thorn external catheter 403 and the thorn inner catheter 408 can move with respect to the second control part 502 under the drive of the first control part 501. It can be understood that the distance between the second control part 502 and the first control part 501 changes according to the relative movement of the two control parts. In addition, the first control part 501 has a hollow channel for the guide wire 409 to pass through.

Figure 11:
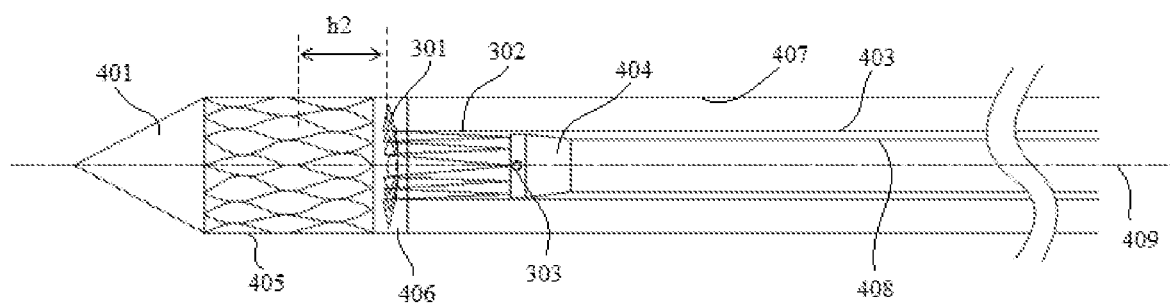
FIG. 11 is a schematic view illustrating another structure of the front end part after the thorn structure and the valve stent are loaded in the delivery device in FIG. 6.

As shown in FIG. 6 and FIG. 7, when the thorn structure 300 is loaded into the first catheter assembly 41, the thorn lug 303 of the thorn structure 300 is against the first fixing head 404, and the thorn external catheter 403 is wrapped around the outside of the thorn stent 310, exposing the thorn 301 (shown in FIG. 11). When the valve stent 200 is loaded into the second catheter assembly 42, the valve stent lug 203 of the valve stent 200 is against the second fixing head 406, and the valve stent external catheter 405 is wrapped around the outside of the valve stent 200.

The valve prosthesis in the above-mentioned embodiment can reduce the diameter of the delivery catheter and the size of the valve stent by manufacturing and implanting the valve stent and the thorn structure separately, so as to facilitate the clinical implanting through the aortic arch or through the curved path of the mitral femoral vein, thus greatly reducing the delivery difficulty and the risk of vascular injury, thus effectively avoiding the risk of complications. In addition, the prick structure of the mechanical stent can effectively solve the problem that the existing valve stent cannot reach the ideal bending angle due to the bending angle fixation, and effectively avoid the risk of fracture in the manufacturing process and fatigue fracture in the human body caused by the large bending angle and deformation, so as to greatly improve the production efficiency. It can also effectively reduce production costs.

Figure 9:
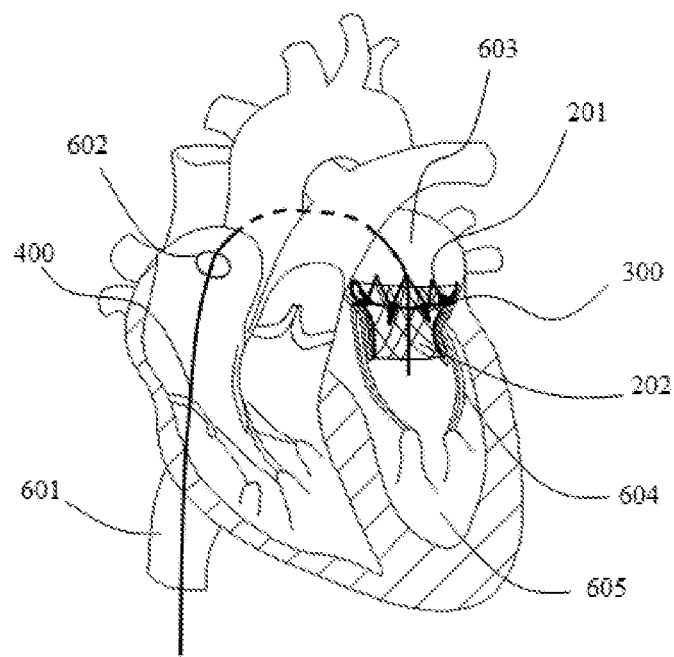
FIG. 9 is a schematic view illustrating the structure when the delivery device is loading.

FIG. 9 is a schematic view illustrating the structure when the delivery device is loading. As shown in FIGS. 6~11, when loading and releasing the valve prosthesis with the delivery device, the valve prosthesis can be implanted step by step loading and releasing, In one embodiment:

Step S11, use the second control part 502 in the control handle 500 to successively withdraw the second catheter assembly 42 in the delivery device to expose the first catheter assembly 41 used for loading the thorn structure 300 (as shown in FIG. 6).

Step S12, the first control part 501 in the control handle 500 is used to withdraw the thorn external catheter 403 of the first catheter assembly 41 to expose the first fixing head 404 used for fixing the thorn structure 300.

Step S13, after loading and fixing the thorn lug 303 in the thorn structure 300 on the first fixing head 404, moving the thorn external catheter 403 forward so that the front end of the thorn external catheter 403 contacts the thorn 301 in the thorn structure 300. At this time, the thorn stent 302 in the thorn structure 300 is in a compressed state, and then the loading operation of the thorn structure 300 is completed (as shown in FIG. 6).

Step S14, keep pushing forward the second fixing head 406, so that the second fixing head 406 can block (or sleeve) the position of the thorn 301 in the loaded thorn structure 300, loading and fixing the valve stent lug 203 on the second fixing head 406, and then pushing forward the valve stent external catheter 405 until the valve stent 200 is completely compressed into the valve stent external catheter 405. At this time, the front end of the compressed valve stent 200 (i.e. one end that far away from the valve stent lug 203) leans is against the conical head 401 to complete the loading operation of the valve stent 200 (as shown in FIG. 7).

Further, after the above steps s11-s14 are carried out, the structure as shown in FIG. 8 can be formed. Since the thorn external catheter 403 and the thorn inner catheter 408 in the first catheter assembly 41, and the valve stent external catheter 405 and the valve stent inner catheter 407 in the second catheter assembly 42 can be made of polymer flexible materials, the delivery catheter 400 can be bent arbitrarily. In one embodiment, the back end of the delivery catheter 400 is connected with the control handle 500, and the front end is connected with the conical head 401, so as to facilitate the implantation of the valve prosthesis and avoid the injury of the blood vessel wall.

Step S15, based on the structure shown in FIG. 7 and FIG. 8, as shown in FIG. 9, guide wire 409 is implanted into left ventricle 605 through femoral vein, and then delivery catheter 400 is punctured into oval fossa 602 through inferior vena cava 601 into left atrium 603 to reach the position of mitral valve 604.

Step S16, after the delivery catheter 400 is delivered to a suitable position, the valve stent external catheter 405 is withdrawn so that the valve stent 200 is slowly released from the valve stent external catheter 405. When the end of the valve stent external catheter is close to the valve stent lug 203, the first control part 501 is pushed forward by h1 relative to the second control part 502. When the distance h1 is equal to the distance h2 between the thorn 301 and the fixing hole 204 (i.e., h1=h2), the thorn 301 can just penetrate the fixing hole 204 and pierce into the human body tissue. During the pushing process, the doctor can observe the specific position of the first control part 501 through the angiography, so as to ensure that the thorn 301 is accurately released to the designated position (as shown in FIG. 10 and FIG. 11).

Step S17, withdraw the thorn external catheter 403 to release the thorn 301 slowly from the thorn inner catheter 41, and after the thorn 301 is completely released and pierced into the cardiac cavity tissue through the fixing hole, separate the lug 303 of the thorn 301 from the first fixing head 404, and then release the thorn structure 300 completely.

Step S18, withdraw the valve stent external catheter 405, and completely separate the valve stent lug 203 from the second fixing head 406, so as to completely separate the valve stent 200, that is, at this time, the release of the valve stent of the cardiac valve prosthesis is completed, and the implanted artificial valve 100 starts to work instead of the primary valve.

Step S19, withdraw the delivery catheter 400.

In the above-mentioned embodiment, by loading the thorn structure and the valve stent into the same delivery system step by step, and when the valve stent is released but the valve stent lug is not completely separated from the delivery device, that is, when the valve stent lug is still connected with the fixing head on the delivery device, the thorn structure is released, because the valve leaf (i.e. artificial valve) fixed on the valve stent has begun to work instead of the primary valve leaf, so there is enough time for the release of thorns. After the thorns are anchored stably, the thorn structure is released completely, and then the valve stent is released continuously until the valve stent is separated from the delivery device, and the delivery device is withdrawn, so as to complete the implantation of the cardiac valve prosthesis.

In a summary, the cardiac valve prosthesis, the delivery device and the method of loading and releasing the cardiac valve prosthesis recorded in the embodiment of the present disclosure can effectively reduce the size of the valve stent and the delivery catheter of the delivery device, enhance the stability of the fixation by manufacturing and implanting and releasing the main body of the valve stent (i.e. the valve stent 200) and the anchoring structure (i.e. the thorn structure 300) separately. Moreover, the thorn made of degradable materials can effectively avoid the complications caused by permanent invasive fixation and the risk of fracture of the thorn structure.

The above-mentioned embodiments can be combined arbitrarily. In order to make the description concise, all possible combinations of the above embodiments are not described. However, as long as the combination of these embodiments does not conflict, it should be considered as the scope of the description.

The above-mentioned embodiments only express several embodiments of the present disclosure, the description of which is more specific and detailed, but it cannot be understood as the limitation of the scope of the disclosure. It should be noted that for those skilled in the art, without departing from the concept of the present disclosure, several deformations and improvements can be made, all of which belong to the protection scope of the present disclosure. Therefore, the scope of protection of the disclosure patent shall be subject to the appended claims.

What is claimed is:

1. A cardiac valve prosthesis, comprising:
an expandable valve stent provided with multiple fixing holes;
an artificial valve provided on the valve stent; and
a thorn structure comprising an expandable thorn stent and multiple thorns, the valve stent and the thorn structure configured to be set independently,
wherein the thorn structure is located inside the valve stent, and the valve stent and the thorn structure cooperate with each other with no mechanical connectors between each other; and
wherein the multiple thorns are provided on the thorn stent, the size of the thorn stent in a fully expanded state is greater than or equal to the size of the valve stent in the fully expanded state, the position of the multiple thorns on the thorn stent matches the position of the fixing holes on the valve stent, and the size of the multiple thorns on the thorn stent is smaller than the size of the fixing holes on the valve stent, when the cardiac valve prosthesis is implanted into a cardiac chamber, passing through the multiple fixing holes and penetrating tissue in the cardiac chamber so as to fix the valve stent.

2. The cardiac valve prosthesis according to claim 1, wherein the thorn structure further comprises:
a thorn lug provided at a proximal end of the thorn stent and extended toward a central axis of the thorn stent,
wherein the multiple thorns are provided at the distal end of the thorn stent and extended away from the central axis of the thorn stent.

3. The cardiac valve prosthesis according to claim 2, wherein the thorn stent comprises:
multiple connecting rods connected end to end to form a closed chain structure,
wherein any two adjacent connecting rods form a V-shaped structure.

4. The cardiac valve prosthesis according to claim 3, wherein the multiple thorns and the thorn lug are respectively provided at a connection between any two of the multiple connecting rods.

5. The cardiac valve prosthesis according to claim 3, wherein the multiple thorns and the multiple connecting rods are an integral manufacturing structure.

6. The cardiac valve prosthesis according to claim 2, wherein the thorn stent is a mesh structure composed of multiple diamond-shaped grids.

7. The cardiac valve prosthesis according to claim 1, wherein tips of the multiple thorns are conical tips, pyramid tips or prismatic tips, and the tips of the multiple thorns are provided with multiple barb structures.

8. The cardiac valve prosthesis according to claim 1, wherein a material of the multiple thorns is medical biodegradable material.

9. The cardiac valve prosthesis according to claim 8, wherein the medical biodegradable material comprises at least one of polycaprolactone, polylactic acid and polyglycolic acid copolymer.

10. The cardiac valve prosthesis according to claim 1, wherein the multiple fixing holes comprise dense grids arranged along a circumferential direction of the valve stent, and the size of the dense grids is smaller than that of other grids on the valve stent.

11. The cardiac valve prosthesis according to claim 10, wherein the size of the dense grids is ⅓ to ⅙ of that of other grids on the valve stent.

12. The cardiac valve prosthesis according to claim 1, wherein the valve stent comprises an inflow channel part for blood inflow and an outflow channel part for blood outflow, wherein the multiple fixing holes are provided in the inflow channel part or at a junction of the inflow channel part and the outflow channel part,
wherein the multiple fixing holes are distributed along a circumferential direction of the valve stent.

13. A delivery device for loading the cardiac valve prosthesis of claim 1, wherein the delivery device comprises:
a conical head;
a control handle; and
a delivery catheter, the two ends of the delivery catheter being respectively connected with the conical head and the control handle;
wherein the delivery catheter comprises a first catheter assembly and a second catheter assembly sleeved outside the first catheter assembly, the first catheter assembly is used for loading the thorn structure, and the second catheter assembly is used for loading the valve stent, and
wherein the control handle is used to control the first catheter assembly to release the thorn structure in a process of controlling the second catheter assembly to release the valve stent, so that the thorn structure can penetrate the tissues in a cardiac cavity through the multiple fixing holes to fix the valve stent.

14. The delivery device according to claim 13, wherein the control handle comprises a first control part and a second control part, the first control part is connected with the first catheter assembly for controlling the first catheter assembly, and the second control part is connected with the second catheter assembly for controlling the second catheter assembly.

15. The delivery device according to claim 14, wherein the first catheter assembly comprises:
  a soft catheter;
  a thorn external catheter, a proximal end of the thorn external catheter being connected to the first control part;
  a thorn inner catheter provided inside the thorn external catheter, and the proximal end of the thorn inner catheter being connected to the first control part; and
  a first fixing head, one end of the first fixing head being connected to the thorn inner catheter, the other end being connected to the conical head through the soft catheter,
  wherein the first fixing head is used for loading the thorn structure.

16. The delivery device according to claim 15, wherein the first control part comprises:
  a first control structure connected with the thorn external catheter for controlling movement of the thorn external catheter relative to the thorn inner catheter.

17. The delivery device according to claim 14, wherein the second catheter assembly comprises:
  a valve stent external catheter, a proximal end of the valve stent external catheter being connected with the second control part;
  a valve stent inner catheter provided inside the valve stent external catheter, a proximal end of the valve stent inner catheter being connected with the second control part; and
  a second fixing head fixedly connected with the valve stent inner catheter,
  wherein the second fixing head is used for loading the valve stent.

18. The delivery device according to claim 17, wherein the second control part comprises:
  a second control structure connected with the valve stent external catheter for controlling movement of the valve stent external catheter relative to the valve stent inner catheter.

* * * * *